United States Patent [19]

Nalewajek et al.

[11] Patent Number: 4,548,763

[45] Date of Patent: Oct. 22, 1985

[54] PREPARATION OF VINYLPHOSPHONATE DIESTERS

[75] Inventors: David Nalewajek, West Seneca; David S. Soriano, Cheektowaga; Ralph J. Borowski, Depew, all of N.Y.

[73] Assignee: Allied Corporation, Morris Township, Morris County, N.J.

[21] Appl. No.: 557,782

[22] Filed: Dec. 5, 1983

[51] Int. Cl.$^4$ .............................................. C07F 9/40
[52] U.S. Cl. ..................................... 260/989; 260/956
[58] Field of Search ......................................... 260/989

[56] References Cited

U.S. PATENT DOCUMENTS

| | | | |
|---|---|---|---|
| 2,535,172 | 12/1950 | Tawney | 260/968 |
| 2,535,173 | 12/1950 | Tawney | 260/968 |
| 2,535,174 | 12/1950 | Tawney | 260/968 |
| 2,535,175 | 12/1950 | Tawney | 260/968 |
| 2,570,503 | 10/1951 | Tawney | 260/968 |
| 2,651,656 | 9/1953 | Ladd et al. | 260/970 |
| 2,784,169 | 3/1957 | Slocombe | 260/45.7 |
| 2,784,171 | 3/1957 | Chadwick | 260/45.75 |
| 2,784,206 | 3/1957 | Chadwick | 260/429 |
| 3,493,639 | 2/1970 | Tavs | 260/969 |
| 3,705,214 | 12/1972 | Martin | 260/969 |
| 3,962,201 | 6/1976 | Dulog et al. | 526/193 |
| 4,129,710 | 12/1978 | Jin | 526/278 |

OTHER PUBLICATIONS

Bûraca et al., "La Chimica E L'Industria", vol. 60, No. 6, (1978), pp. 530–534.
Young et al., "Inorganic Syntheses", vol. 17, (1978), pp. 75–77.
Chabrier et al., "Chem. Abs.", vol. 62, (1965), 2790e.
Arcus et al., "J. Chem. Soci.," (1956), pp. 4607–4612.

Primary Examiner—Anton H. Sutto
Attorney, Agent, or Firm—Arthur J. Plantamura; Jay P. Friedenson; Richard C. Stewart

[57] ABSTRACT

Allylphosphonate diesters are converted to vinyl phosphonate diesters by isomerization with a catalytic amount of a ruthenium catalyst. Vinyl phosphonate derivatives are produced directly from an organo pentavalent phosphorus compound. In a particular reaction conversion of allylic phosphonate diesters to vinylic phosphonate diesters is accomplished by the transition metal mediated isomerization of the alkylphosphonate derivatives with tetrakis(triphenylphosphine)dihydrido ruthenium(II).

10 Claims, No Drawings

PREPARATION OF VINYLPHOSPHONATE DIESTERS

DESCRIPTION

This invention relates to a process whereby allylic pentavalent organo phosphorus compounds can be catalytically converted to vinylic organopentavalent phosphorus compounds.

BACKGROUND OF THE INVENTION

Esters of vinylphosphonic acid serve as useful synthons, i.e. precursors, for the preparation of agriculturally active compounds. Uses range from plant growth regulators to phosphatase inhibitors to pesticides. The versatility of this intermediate material resides in the reactivity of the vinylic group towards nucleophiles. The application of this reactivity via reaction with alcohols, thiols, amines, nitroalkanes or active methylene compounds results in this wide class of agricultural chemicals.

Vinylphosphonates also undergo Diels-Alder reactions with dienes. Polymerizaton or co-polymerization has resulted in the preparation of heat and light stabilizers for polymers as well as flame retardant or shrinkage retardant additives.

Heretofore, synthetic approaches to the formation of vinylic phosphonates have centered on direct replacement of the vinylic halide with trivalent phosphorous esters. With the exception of α,β-unsaturated systems, reactions involving simple Michaelis-Arbuzov reaction conditions have failed. Similarly, reactions involving transition metal salts as catalysts have found greater utility but are still limited to the reaction of aromatic or vinylic halides with phosphites or similar trivalent phosphorus compounds as disclosed, for example, in U.S. Pat. No. 3,493,639. Because of apparent severe reaction conditions involved in these syntheses, industrial aplication of these reaction products have been limited.

It is thus apparent that a need exists for an improved practical and efficient method for the preparation of vinyl phosphonate diesters.

SUMMARY OF THE INVENTION

In accordance with the invention, a novel method is provided for the production of vinylic phosphonate derivatives directly from an organo pentavalent phosphorus compound and, in particular, for the conversion of allylic phosphonate diesters to vinylic phosphonate diesters via the transition metal catalyzed isomerization of the alkylphosphonate derivatives with a ruthenium catalyst, such as tetrakis(triphenylphosphine)dihydrido ruthenium (II).

The method of the present invention, obviates the difficulties associated with the Michaelis-Arbuzov reaction and affords a simple and non-expensive method to obtain vinylic phosphonate diesters in shorter reaction time and higher yield by using tetrakis(triphenylphosphine)dihydrido ruthenium(II).

DESCRIPTION OF THE PREFERRED EMBODIMENTS

In accordance with the invention, vinylic phosphonate diesters are prepared from allylic phosphonate diesters by a mechanism that avoids the difficulties associated with the Michaelis-Arbuzov reaction and permits a very simple and non-expensive method to obtain vinylic phosphonate diesters in shorter reaction times and in higher yield accomplished by using a ruthenium catalyst. Especially good results are obtained when the ruthenium catalyst used is tetrakis(triphenylphosphine)dihydrido ruthenium(II). The isomerization of an allyl phosphonate moiety to a vinyl phosphonate moiety according to the present invention provides an easy access to a class of compounds of wide industrial application.

Pursuant to the invention, an allyl phosphonate diester is catalytically converted to a vinyl phosphonate diester by use of the metal hydride of the transition metal ruthenium. The reaction may be described by the following equation:

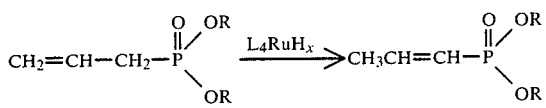

wherein L is a triaryl phosphine ligand, preferably triphenyl phosphine; X represents the number of hydrido moieties in the metal complex, preferably two, and R is an alkyl group of one to seven carbon atoms, preferably methyl or ethyl.

It has been discovered that this reaction may be conducted so as to obtain a high yield of conversion of allyl phosphonate diesters to vinyl phosphonate diesters by contacting the allyl phosphonate directly with the catalyst. It has also been found that the reaction may also proceed in the presence of a solvent inert to substitution at the transition metal center. This required inertness of the solvent to the reaction is essential to avoid deactivation by poisoning the catalyst. Suitable solvents which have been discovered to conform to this requirement include benzene, its monoalkylated derivative, such as and toluene, etc., and its dialkylated derivatives such as xylene, etc. Obviously, equivalent solvents conforming to the definition may also be employed.

The transition metal hydride catalyst, tetrakis(triphenylphosphine)dihydrido ruthenium(II), $Ru(P[C_6H_5]_3)_4H_2$, as employed in this reaction may be prepared in a known manner as described for example in Inorganic Synthesis 17 p. 75 (1978). Similarly, the allyl phosphonates used as starting materials in the process of this invention are also obtainable according to known methods as disclosed for example in Compt. Rend 259, 2244-7 (1964). In general, the reaction of the ruthenium hydride catalyst with the allyl phosphonate diester is conducted under inert atmosphere (argon or nitrogen) and at ambient temperature or at temperatures between 100°–150° C. when no solvent is used. These moderate conditions have been found to be satisfactory for conducting the reaction. An alternative method involves the addition of the catalyst to a solution of the allyl phosphonate diester in a solvent of the kind described above. For this process, the reaction mixture is brought to the refluxing temperature of the solvent used. After heating for a suitable period of time, preferably 7–8 hours, the contents of the reaction vessel are vacuum distilled, and the products analyzed by standard techniques. Yields of vinylphosphonate diesters typically ranged from 90–95% with the only other identifiable material in the reaction product determined to be starting phosphonate.

The reactants, can also be stirred at room temperature in a suitable solvent. After 6–8 hours, the solvent is removed under reduced pressure and the product separated from starting phosphonate by vacuum distillation. Yields were typically lower by this process and ranged from 75–85%; in any event, yields at a practical level of at least 70% are allowable.

The following examples are presented to illustrate the process of this invention. It will be understood, however, that although the examples may describe in detail certain preferred operating conditions of the invention they are given primarily for purposes of illustration and the invention in the broader aspect is not limited thereto.

EXAMPLE 1

5 g ($3.3 \times 10^{-2}$ mol) of O,O-dimethylallyl phosphonate and 0.076 g ($6.6 \times 10^{-5}$ mol) of tetrakis(triphenylphosphine)dihydrido ruthenium(II) were placed in a 20 mL round bottom flask and heated to 150° C. The mole ratio of substrate to catalyst was 500/1. After 1 hour the isomerization process began and the formation of 1-methyl,2-vinyl,O,O-dimethylphosphonate was observed by NMR. Heating was continued for an additional 6 hours after which time the reaction was terminated and the product vacuum distilled. A conversion of 92% of the original allyl phosphonate to the vinyl phosphonate was obtained. NMR (d-CHCl$_3$, TMS) 6.8(m), 5.63(m) 3.73(s), 3.60(s), 1.93(m).

EXAMPLE 2

Reaction conditions are identical to Example 1 except that 10 mL of toluene was added to the reaction flask and the mixture heated to 100° C. After 8 hours, 87% conversion to vinyl phosphonate had occurred.

EXAMPLE 3

Reaction conditions were identical to Example 1 except that 10 mL of benzene was added to the reaction flask and the mixture heated to 80° C. After 6 hours, 94% conversion to vinyl phosphonate had occurred.

EXAMPLE 4

Reaction conditions were identical to Example 1 except that 10 mL of o-xylene was added to the reaction flask and the mixture heated to 140° C. After 7 hours, 95% conversion to vinyl phosphonate had occurred.

EXAMPLE 5

Reaction conditions were identical to Example 1 except that 10 mL of m-xylene was added to the reaction flask and the mixture heated to 138° C. After 7 hours, 95% conversion to vinyl phosphonate had occurred.

EXAMPLE 6

Reaction conditions were identical to Example 1 except that 10 mL of p-xylene was added to the reaction flask and the mixture heated to 135° C. After 7 hours, 90% conversion to vinyl phosphonate had occurred.

EXAMPLE 7

Reaction conditions were identical to Example 1 except that 10 mL of a commercially available mixture of o,m,p-xylene was added to the reaction flask and the mixture heated to 137°–140° C. After 7 hours, 91% conversion of the allyl phosphonate to vinyl phosphonate had occurred.

EXAMPLE 8

Reaction conditions were identical to Example 1 except that 10 mL of ethylbenzene was added to the reaction flask and the mixture heated to 136° C. After 8 hours, 94% conversion to vinyl phosphonate had occurred.

EXAMPLE 9

Reaction conditions were identical to Example 1 except that 10 mL of o-diethylbenzene was added to the reaction flask and the mixture heated to 150° C. After 7 hours, 88% conversion of the allyl phosphonate had occurred.

EXAMPLE 10

Reaction conditions were identical to Example 1 except that 10 mL of p-diethylbenzene was added to the reaction flask and the mixture heated to 150° C. After 7 hours, 88% conversion of the allyl phosphonate to vinyl phosphonate had occurred.

EXAMPLE 11

Reaction conditions were identical to Example 1 except that 10 mL of m-diethylbenzene was added to the reaction flask and the mixture heated to 150° C. After 7 hours, 85% conversion of the allyl phosphonate had occurred.

EXAMPLE 12

Reaction conditions were identical to Example 1 except that 10 mL of diethylbenzenes (i.e., a commercial mixture of o,m,p-diethylbenzene) was added to the reaction flask and the mixture heated to 150° C. After 7 hours, 86% conversion of the allyl phosphonate had occurred.

EXAMPLE 13

Reaction conditions were identical to Example 1 except that 10 mL of propylbenzene was added to the reaction flask and the mixture heated to 160° C. After 7 hours, 90% conversion of the allyl phosphonate had occurred.

EXAMPLE 14

5 g ($3.3 \times 10^{-2}$ mol) of O,O-dimethylallylphosphonate and 0.076 g ($6.6 \times 10^{-5}$ mol) of tetrakis-(triphenylphosphine)dihydrido ruthenium(II) dissolved in 10 mL of toluene were placed in a 20 mL round bottom flask. The mixture was stirred for 6 h at ambient temperature and the solvent removed under reduced pressure. The product was distilled at 90°–100° C. at 0.1 mmHg to yield 83% of 1-methyl,2-vinyl,O,O-dimethylphosphonate.

EXAMPLE 15

Reaction conditions were identical to Example 14 except that 10 mL of benzene was added to the reaction flask. After 8 hours, 85% conversion to the vinyl phosphonate had occurred.

EXAMPLE 16

Reaction conditions were identical to Example 14 except that 10 mL of o-xylene was added to the reaction flask. After 8 hours, 80% conversion to the vinyl phosphonate had occurred.

EXAMPLE 17

Reaction conditions were identical to Example 14 except that 10 mL of m-xylene was added to the reaction flask. After 8 hours, 80% conversion to the vinyl phosphonate had occurred.

EXAMPLE 18

Reaction conditions were identical to Example 14 except that 10 mL of p-xylene was added to the reaction flask. After 8 hours, 78% conversion to the vinyl phosphonate had occurred.

EXAMPLE 19

Reaction conditions were identical to Example 14 except that 10 mL of xylenes was added to the reaction flask. After 7 hours, 77% conversion to the vinyl phosphonate had occcurred.

EXAMPLE 20

Reaction conditions were identical to Example 14 except that 10 mL of ethylbenzene was added to the reaction flask. After 7 hours, 78% conversion of the allyl phosphonate to vinyl phosphonate had occurred.

EXAMPLE 21

Reaction conditions were identical to Example 14 except that 10 mL of o-diethylbenzene was added to the reaction flask. After 7 hours, 75% conversion of the allyl phosphonate to vinyl phosphonate had occurred.

EXAMPLE 22

Reaction conditions were identical to Example 14 except that 10 mL of m-diethylbenzene was added to the reaction flask. After 7 hours, 75% conversion of the allyl phosphonate to vinyl phosphonate had occurred.

EXAMPLE 23

Reaction conditions were identical to Example 14 except that 10 mL of p-diethylbenzene was added to the reaction flask. After 7 hours, 74% conversion of the allyl phosphonate to vinyl phosphonate had occurred.

EXAMPLE 24

Reaction conditions were identical to Example 14 except that 10 mL of diethylbenzenes was added to the reaction flask. After 7 hours, 73% conversion of the allyl phosphonate to vinyl phosphonate had occurred.

EXAMPLE 25

Reaction conditions were identical to Example 14 except that 10 mL of propylbenzene was added to the reaction flask. After 7 hours, 75% conversion of the allyl phosphonate to vinyl phosphonate had occurred.

It will be apparent that various modifications may be effected without departing from the scope of the invention; accordingly, the several details disclosed as illustrative are not to be construed as placing limitations on the invention except as may be recited in the appended claims.

What is claimed is:

1. A method for the preparation of a vinylic phosphonate diester of the formula:

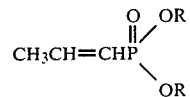

from a corresponding allyl phosphonate diester of the general formula

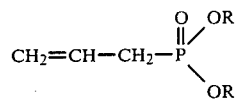

wherein R is an alkyl substituent of 1 to 7 carbon atoms, which comprises:
(a) reacting said allyl phosphonate diester in the presence of a catalytic amount of a ruthenium metal hydride until at least 85% isomerization of starting allyl phosphonate diester is effected.

2. A method according to claim 1 wherein the catalyst is tetrakis(triphenylphosphine)dihydro ruthenium-(II), $(P[C_6H_5]_3)_4RuH_2$.

3. A method according to claim 1 wherein the reaction temperature is maintained between 100°–150° C.

4. A method according to claim 1 wherein the solvent is selected from the group consisting of benzene and monoalkylated and dialkylated substituted benzenes.

5. A method according to claim 1 wherein the reaction is conducted at ambient temperature.

6. A process according to claim 1 wherein the temperature of the reaction is performed at the reflux temperature of the solvent.

7. A process according to claim 1 wherein the reaction product is isolated by vacuum distillation.

8. A method according to claim 2 wherein the reaction is performed at the reflux temperature of the solvent.

9. A method according to claim 2 wherein the reaction temperature is maintained between 100°–150° C.

10. A method according to claim 2 wherein the reaction is conducted at ambient temperature.

* * * * *